United States Patent [19]

Maxfield et al.

[11] Patent Number: 4,597,969

[45] Date of Patent: Jul. 1, 1986

[54] STABILIZATION OF UNSTABLE DRUGS OR FOOD SUPPLEMENTS

[75] Inventors: Howard C. Maxfield, Broxbourne; Anthony J. Phillips, Ware; Richard J. Yarwood, Stevenage Old Town, all of England

[73] Assignee: Merck Sharp & Dohme, Hoddesdon, United Kingdom

[21] Appl. No.: 462,115

[22] Filed: Feb. 1, 1983

Related U.S. Application Data

[63] Continuation-in-part of Ser. No. 365,418, Apr. 5, 1982, abandoned.

[51] Int. Cl.$^4$ .................. A61K 33/08; A61K 31/70; A61K 31/71; A61K 31/725
[52] U.S. Cl. ........................... 424/157; 514/23; 514/37; 514/56; 514/450
[58] Field of Search ............... 424/180, 181, 183, 157; 514/23, 37, 56

[56] References Cited

U.S. PATENT DOCUMENTS

| | | | |
|---|---|---|---|
| 3,627,885 | 12/1971 | Rondelet et al. | 424/227 |
| 3,853,842 | 12/1974 | Kishi et al. | 260/210 |
| 3,950,360 | 4/1976 | Aoki et al. | 260/343.2 R |
| 4,024,251 | 5/1977 | Maiese et al. | 424/181 |
| 4,048,268 | 9/1977 | Ludwig | 264/15 |
| 4,092,473 | 3/1978 | Okamoto et al. | 536/17 |
| 4,144,352 | 3/1979 | Putter | 424/279 |
| 4,199,569 | 4/1980 | Chabala et al. | 424/180 |
| 4,219,572 | 8/1980 | Jackman | 426/69 |

FOREIGN PATENT DOCUMENTS 2056986  3/1981  United Kingdom .

*Primary Examiner*—Jerome D. Goldberg
*Assistant Examiner*—John W. Rollins
*Attorney, Agent, or Firm*—David L. Rose; Hesna J. Pfeiffer

[57] ABSTRACT

A granulation method involving polysaccharide gelling agents, e.g., alginic acid, and a metal salt, e.g., magnesium salt is developed for the stabilization of heat and/or moisture sensitive drugs or food supplements such as Efrotomycin, avermectins, milbemycins, mocimycin and other drugs. It has been found that the granules so obtained can be incorporated into various formulations without substantial decomposition.

19 Claims, No Drawings

STABILIZATION OF UNSTABLE DRUGS OR FOOD SUPPLEMENTS

This application is a continuation in-part of Ser. No. 365,418, filed Apr. 5, 1982, now abandoned.

BACKGROUND OF THE INVENTION

The present invention relates to the stabilization of drugs including antibiotics and food supplements. Particularly, it concerns the granulation of Efrotomycin, milbemycins, tylosin derivatives, e.g., A.I.V. (3-acetyl-4″-isovaleryl tylosin), antibiotics B-5050 and tetrahydro-B-5050, Ivermectin, mocimycin, goldinomycin and the like in alginic acid and magnesium hydroxide. It has been found that the granules so obtained exhibit unexpectedly enhanced stability and can be incorporated into various formulations without substantial decomposition. When the drugs or food supplements are administered to animals, the formulations include animal feed, pellets or feed premix.

Efrotomycin (FR-02A) is a new antibiotic which also exhibits growth-promoting activity. It is effective against both gram-positive and gram-negative bacteria and accordingly is useful in the treatment of a broad spectrum of infections in animals. Efrotomycin is disclosed in U.S. Pat. No. 4,024,251 issued May 17, 1977 to Maiese and Wax. The antibiotic is isolated from the fermentation broth of *Streptomyces lactamfuran* by solvent extraction and is believed to have the molecular structure as follows:

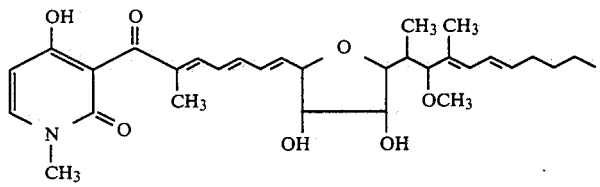
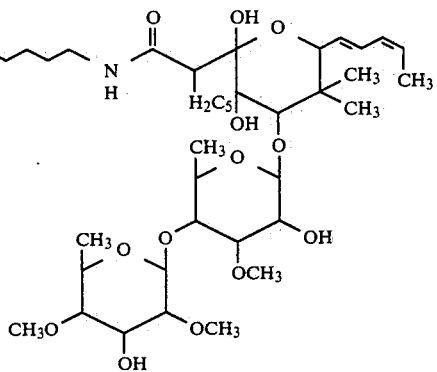

The physical properties of Efrotomycin (FR-02A) are summarized as follows: Elemental analysis:
C 60.98%
H 7.60%
N 2.60%

The corresponding empirical formula $C_{59}H_{90}N_2O_{21}$ is consistent with monohydrated FR-02A. This is in agreement with a molecular weight of about 1168 of the sodium complex of FR-02A determined by field desorption mass spectrometry. Further mass spectroscopic study of FR-02A determined the molecular weight 1144 for the uncomplexed compound corresponding to the empirical formula $C_{59}H_{88}N_2O_{20}$.

FR-02A as the ammonium salt is soluble in alcohol and chloroform. It is moderately soluble in water at pH 7.0 or higher. A U.V. spectrum of the ammonium salt in water showed:

max. 233 nm: $E_1\,_{cm}^{1\%} = 320$
max. 328 nm: $E_1\,_{cm}^{1\%} = 180$

After further purification FR-02A in the free acid has the following U.V. spectrum in methanol—0.05M phosphate buffer pH 6.85 (20:80):

max. 325 nm: $E_1\,_{cm}^{1\%} = 317$
max. 230 nm: $E_1\,_{cm}^{1\%} = 554$
max. 219 nm: $E_1\,_{cm}^{1\%} = 556$ Specific optical rotation of FR-02A sodium salt is $[\alpha]_D^{20} - 56.6 \pm 0.5$ (C=1, MeOH).

The nuclear magnetic resonance spectrum of antibiotic FR-02A was obtained at 100 MHz with $CDCl_3$ as the solvent and tetramethylsilane (TMS) as the internal standard. Representative features of the spectrum were Doublets at 1.21(3H), 1.31(3H), 1.74(3H), 4.63(1H), 4.87(1H), 5.94(1H) and 7.32(1H) ppm. Overlapping signals of 4 other C-methyl groups centered at about 0.94 ppm; Singlets at 1.65(3H), 2.02(3H), 3.15(3H), 3.42(3H), 3.45(3H), 3.54(3H), and 3.58(3H) ppm.

The infrared absorption spectrum of antibiotic FR-02A in a Nujol mull exhibits characteristic absorption at the following wave lengths expressed in reciprocal centimeters:

Broad Band at: 3400
Strong bands at: 1640, 1460, 1380, 1080, 1020
Prominent bands at: 1550, 1505, 1240, 1195, 940, 860, 720, 620.

Further characteristics of FR-02A as well as the process for isolating the antibiotic are described in U.S. Pat. No. 4,024,251 and are herein incorporated by reference.

Efrotomycin is found to be unstable at elevated temperatures especially in the presence of moisture and feed components. However, in administering Efrotomycin to animals, it is most convenient and economic to include the antibiotic-growth promotor agent in premixes for animal feeds. Usually a premix is blended into animal feeds followed by injection of steam resulting in a final temperature of 85°–100° C. The mixing process takes about 2–15 minutes. The agglomerates may be either cooled and dried to produce a mash feed or extruded to give pelleted feed. In other words, Efrotomycin must be stabilized first before it can be incorporated into animal feeds.

Accordingly, it is desirable to develop a method of formulation for the stabilization of Efrotomycin to enable the inclusion thereof in animal feed.

One of the commonly used methods of formulation for stabilization is granulation because of ease, efficiency and consequently lower cost. Methods described in the literature include granulation with specific inorganic materials (U.S. Pat. No. 3,627,885, Dec. 14, 1971) or with starch (U.S. Pat. No. 4,048,268, Sept. 13, 1977). Neither of these techniques were suitable for Efrotomycin.

Granulation with inorganic salts, particularly those of magnesium did result in some stabilization but unexpected synergistic improvement occurred when polysaccharides were incorporated into the formulation as can be seen from table 1.

TABLE 1

The effect of the addition of polysaccharide gelling agents to magnesium hydroxide on the stability of efrotomycin stored in animal feed at 50° C., (all contain 5% efrotomycin and magnesium hydroxide:gum in the weight ratio 1:1).

| Polysaccharides | Magnesium hydroxide | Storage time | % of initial remaining |
|---|---|---|---|
| — | — | 17 days | 12 |
| — | present | 25 days | 56 |
| Guar gum (anionic) | present | 28 days | 71 |
| Guar gum (nonionic) | present | 28 days | 79 |
| Guar gum (cationic) | present | 28 days | 55 |
| Tragacanth | present | 28 days | 68 |
| Acacia | present | 28 days | 81 |
| Alginic acid | present | 35 days | 100 |
| Calcium alginate | present | 56 days | 82 |
| Sodium alginate | present | 30 days | 69 |
| Maize starch | present | 14 days | 90 |
| Locust Bean gum | present | 14 days | 83 |
| Agar-agar | present | 14 days | 80 |

For efrotomycin incorporation of alginic acid gives the best stabilization although all the polysaccharides including those listed in Table 1 and xanthan gum, karaya gum, gum ghatti, and carrageenan offer significant protection.

In case of efrotomycin, the ratio of alginic acid to magnesium hydroxide is important as can be seen in table 2.

TABLE 2

The effect of alginic acid - magnesium hydroxide ratio on the stability of efrotomycin stored in animal feed at 50° C. (all contain 10% efrotomycin).

| % Magnesium hydroxide w/w | % Alginic acid w/w | % of initial remaining after 4 months storage |
|---|---|---|
| 90 | — | 26 |
| 75 | 15 | 73 |
| 60 | 30 | 91 |
| 45 | 45 | 93 |
| 30 | 60 | 100 |
| 15 | 75 | 75 |
| — | 90 | 37 |

It should be noted that the method of the present invention is not limited to Efrotomycin. Any other unstable animal drugs or food supplements may be incorporated into animal feeds or other formulations including human drug formulations according to the formula and process described herein. Particularly, for example, the following drugs:

(1) Ivermectin: a potent antiparasitic agent disclosed in U.S. Pat. No. 4,199,569.

(2) Milbemycins (antibiotics B-41): antibiotics characterized in U.S. Pat. Nos. 4,144,352; 3,950,360; and British Patent Specification No. 2,056,986.

(3) Tylosin and derivatives, e.g., A.I.V.: antibiotics disclosed in U.S. Pat. No. 4,092,473. A.I.V. is the 3-acetyl-4"-isovaleryl derivative ($R_1$ is acetyl and R is isovaleryl in formula I) of tylosin.

(4) Antibiotics B-5050 and tetrahydro-B-5050: disclosed in U.S. Pat. No. 3,853,842.

(5) Mocimycin dihydromocimycin, antibacterial agents disclosed in U.S. Pat. Nos. 3,927,211 and 4,062,948.

(6) Goldinomycin disclosed in U.S. Pat. No. 3,657,421.

The physical characterization, the biological activity as well as the isolation of the above-identified drugs are herein incorporated by reference.

It has been found that these drugs may also be stabilized by granulation with a polysaccharide gelling agent especially alginic acid blended with an inorganic salt, particularly metal oxides or hydroxides such as magnesium hydroxide. The granules may be incorporated into feed, tablets, capsules, or other formulations.

SUMMARY OF THE INVENTION

The present invention concerns a method of granulation for the stabilization of unstable or heat-sensitive animal drugs or food supplements, such as Efrotomycin, tylosin and derivatives (A.I.V.), milbemycins, avermectins such as Ivermectin, mocimycin, goldinomycin and the like. The granulation enables the incorporation of these drugs or food supplements into animal feeds or other formulations without substantial decomposition.

Accordingly, it is the object of this invention, to
(1) develop a granulation method which will produce sufficiently stable granules for inclusion of unstable drugs or food supplements in animal feeds, or other human and animal formulations;
(2) provide a novel stable formula or composition containing one or more of the granulated drugs or food supplements which is resistant to heat, humidity, and other adverse conditions; and
(3) apply the formula and process equally to other unstable human or animal drugs or food supplements for inclusion in feed, tablets or capsules or other suitable formulations.

DETAILED DESCRIPTION OF THE INVENTION

The stabilizing granulation formula of the present invention comprises:
(a) 0.1 to 70 parts by weight of an active compound especially Efrotomycin, A.I.V. or Ivermectin;
(b) 10 to 80 parts by weight of a polysaccharide gelling agent especially guar gums (natural or synthetic), tragacanth, acacia, alginic acid and its salts and derivatives, starch, locust bean gum, agar-agar, xanthan gum, karaya gum, gum ghatti and carrageenan or a mixture thereof; and
(c) 10 to 80 parts by weight of a metal salt especially an oxide, a hydroxide, a carbonate or a silicate of aluminum, calcium or magnesium, for example, magnesium hydroxide.

In a preferred embodiment, the formula comprises:
(a) 2-40 parts by weight of an active compound;
(b) 20-50 parts by weight of alginic acid; or calcium alginate or a combination thereof in the ratio 2-3 parts of alginic acid to 2-3 parts of calcium alginate; and
(c) 20-85 parts by weight of a metal oxide or hydroxide.

In the most preferred embodiment of this invention the formula comprises:
(a) 5-35 parts by weight of an active compound;
(b) 15-50 parts by weight of alginic acid; and
(c) 20-80 parts by weight of magnesium hydroxide.

Efrotomycin, while it is unstable in the below described feeds and feed additives, does not appear to be unstable to water alone. Thus, the instant process is not a strict protection method against hydrolysis. The instant formulation protects antibiotics against deterioration in the presence of feeds. Applicants do not wish to be bound by theory, but this may be accomplished by isolating the compound from the components of feed which cause the deterioration. Thus any compound which is intended for use in feed or feed-like components, and which is unstable in such feeds or feed-like components, but otherwise stable under neutral conditions will benefit from the use of the process of this invention.

For preparing the above defined formulae, the active compound is mixed and agglomerated with other ingredients in the indicated amounts. A sufficient amount of a solvent, for example water; lower alkanol especially $C_{1-6}$ alcohol such as ethanol and methanol; and lower alkanone especially $C_{1-6}$ alkanone such as acetone and diethylketone or a mixture thereof is added and thoroughly dispersed to obtain a wet mass of the desired consistency. Usually, the amount of the solvent needed is about 0.05–2 parts per part by volume of the mixed ingredients. Subsequently, the wet blend is sieved, dried, and screened to yield granules of desired sizes. Alternatively, the mixing can be carried out in a high speed mixer granulator followed by milling and drying in a fluidized bed.

Alternatively, the granulated product defined above may also be obtained by dry compression of the ingredients in the indicated amounts followed by subsequent grinding in order to get the granulated product. Alternatively, the mixed ingredients may be slurried with a suitable solvent and spray dried into granules.

The amount of biologically active compound in the granules may be adjusted up to the most convenient range-e.g., from 0.1 percent to 70 percent by weight—for facilitating the dispersion of the compounds in the feed, and the resulting composition (granules) is then dispersed in any suitable feed, premix substrate or simply used as premix by itself. When the granules are dispersed in animal feed, it is usually incorporated at the rate of about 0.1–10 kg per ton preferably 0.5–2 kg per ton to achieve the desired dose.

Usually the wet-granulation technique is used, the active compound, for example, Efrotomycin, is thoroughly mixed in the indicated amount with alginic acid and magnesium hydroxide. An adequate amount of water or other solvent is added to obtain a wet mass of required consistency. The resulting agglomerate is then granulated by passing through a 16 mesh (1000 μm) screen and dried at about 30°–60° C., preferably at about 45° C. for about 5–48 hours, usually about 15–20 hours. Optionally, the granules may be rescreened through a 30 mesh (595 μm) or other suitable screen to obtain the required size.

Alternatively the mixing can be carried out in a high speed mixer granulator followed by milling and drying in a fluidized bed at about 30° C. to 55° C. for about 1–5 hours.

Although it is not required for performing the invention the formulation may be admixed with suitable inert diluents such as lactose, sucrose, calcium phosphate or micro-crystalline cellulose. Disintegrating agents (e.g. starch or its modifications) or lubricants such as magnesium stearate, stearic acid, polyethylene glycol or talc may be added. The blend may be filled into capsules or compressed into tablets to allow the administration of stabilized drugs, e.g., Ivermectin, as a convenient oral dose.

The following examples are intended to illustrate the preparation of compositions of the invention but they are not to be construed as limiting the scope thereof.

EXAMPLE 1

A wet blend was prepared from mixing the following components:
Efrotomycin (60% pure): 33.33 parts by weight
Alginic acid: 13.33 parts by weight
Magnesium hydroxide: 53.34 parts by weight
Water: sufficient to granulate The wet blend was sieved 16 mesh, dried at 45° C. for 2 hours and then rescreened 30 mesh.

The dried granule was used as a "concentrate" which may then be blended with other inert ingredients, e.g., oiled rice hulls and then incorporated into animal feed at the rate of 0.5–2 kg per ton to achieve the appropriate dose. The stabilization of Efrotomycin was achieved in both the premix and feed as shown below in Table III.

TABLE III

Stability of unprotected and protected Efrothomycin (100 ppm) in feed and pelleted feed. (Concentrate) contains 20% by weight Efrotomycin; mean ± 1 std. deviation)

| Storage Conditions | | Stability in feed (w/w % initial) Efrotomycin (60% pure) | Concentrate | Stability in pelleted feed (w/w % initial) Concentrate |
|---|---|---|---|---|
| 2 wks | 40° C. | — | — | 90.4 ± 13.1 |
|  | 50° C. | — | 87.3 ± 13.3 | 80.7 ± 11.8 |
| 17 days | 40° C. | 22.1 ± 4.5 | — | — |
|  | 50° C. | 11.9 ± 3.3 | — | — |
| 4 wks | 40° C. | 16.5 ± 6.3 | 75.0 ± 8.1 | 88.5 ± 5.7 |
|  | 50° C. | Trace | 73.1 ± 13.3 | 66.5 ± 4.7 |
| 6 wks | 40° C. | 10.5 ± 3.2 | 74.6 ± 4.2 | 98.2 ± 10.2 |
|  | 50° C. | Trace | 78.8 ± 8.1 | 64.3 ± 3.67 |
| 12 wks | 40° C. | — | 106 ± 12.7 | 75.0 ± 8.1 |

Following substantially the same procedure as described above, but substituting for Efrotomycin used therein Ivermectin, there is prepared a stabilized concentrate of Ivermectin.

EXAMPLE 2

A wet blend was prepared from mixing the following components:
Efrotomycin (60% pure): 8.35 parts by weight
Alginic Acid: 18.33 parts by weight
Magnesium hydroxide: 73.32 parts by weight
Water: sufficient to granulate.

The wet blend was treated as described in Example 1 and the stabilization achieved in feed is shown below.

| Storage conditions | | Stability in feed (w/w % initial) |
|---|---|---|
| 4 wks | 40° C. | 91.3 ± 7.9 |
|  | 50° C. | 81.9 ± 8.7 |
| 7 wks | 40° C. | 89.8 ± 8.6 |
|  | 50° C. | 72.1 ± 0.5 |
| 12 wks | 40° C. | 96.0 ± 9.6 |

Following substantially the same procedure as described above, but substituting for Efrotomycin used therein Ivermectin, there is prepared a stabilized concentrate of Ivermectin.

EXAMPLE 3

A wet blend was prepared by mixing the following components.
Efrotomycin: 8.4 parts by weight
Alginic acid: 45.8 parts by weight
Magnesium hydroxide: 45.8 parts by weight
Water: sufficient to granulate The wet blend was treated as described in Example 1 and the stabilization in feed is shown below.

| Storage Conditions | Stability in feed (% initial) |
| --- | --- |
| 9 weeks at 50° C. | 99 ± 9 |

EXAMPLE 4

A wet blend was prepared by mixing the following components.
Efrotomycin: 8.4 parts by weight
Calcium alginate: 45.8 parts by weight
Magnesium hydroxide: 45.8 parts by weight
Water: sufficient to granulate The wet blend was treated as described in Example 1 and the stabilization in feed is shown below.

| Storage Conditions | Stability in feed (w/w % initial) |
| --- | --- |
| 4 weeks at 50° C. | 83 ± 4 |
| 8 weeks at 50° C. | 82 ± 5 |

EXAMPLE 5

A wet blend is prepared by mixing the following components.
Efrotomycin: 8.4 parts by weight
Calcium alginate: 22.9 parts by weight
Alginic acid: 22.9 parts by weight
Magnesium hydroxide: 45.8 parts by weight
Water: sufficient to granulate The wet blend is treated as described in Example 1.

EXAMPLE 6

A wet blend was prepared by mixing the following components.
Efrotomycin: 8.4 parts by weight
Maize starch: 45.8 parts by weight
Magnesium hydroxide: 45.8 parts by weight
Water: sufficient to granulate The wet blend was treated as described in Example 1 and the stablization in feed is shown below.

| Storage Conditions | Stability in feed (w/w % initial) |
| --- | --- |
| 14 days at 50° C. | 90 ± 8 |
| 28 days at 50° C. | 83 ± 9 |
| 56 days at 50° C. | 67 ± 8 |

EXAMPLE 7

A wet blend was prepared by mixing the following components.
Efrotomycin: 8.4 parts by weight
Alginic acid: 45.8 parts by weight
Magnesium oxide: 45.8 parts by weight
Water: sufficient to granulate The wet blend was treated as described in Example 1 and the stabilization in feed is shown below.

| Storage Conditions | Stability in feed (w/w % initial) |
| --- | --- |
| 18 days at 50° C. | 94 ± 2 |
| 56 days at 50° C. | 83 ± 2 |
| 5 months at 50° C. | 82 ± 4 |

EXAMPLE 8

A wet blend was prepared by mixing the following components.
Efrotomycin (60% pure): 33.33 parts by weight
Alginic Acid: 33.33 parts by weight
Magnesium Hydroxide: 33.33 parts by weight
Water: sufficient to granulate The wet blend was treated as described in Example 1 and the stabilization in feed is shown below.

| Storage Conditions | Stability (%) |
| --- | --- |
| In Mash | |
| 12 weeks at 37° C. | 93 ± 6 |
| 12 weeks at 37° C. (Sodium Salt) | 113 ± 7 |
| Pellets | |
| 12 weeks at 37° C. | 84 ± 11 |
| 12 weeks at 37° C. (Sodium Salt) | 93 ± 8 |

EXAMPLE 9

A wet blend was prepared by mixing the following components.
Ivermectin: 1 part by weight
Alginic acid: 49.5 parts by weight
Magnesium hydroxide: 49.5 parts by weight
Water: sufficient to granulate The wet blend was treated as described in Example 1 and the stabilization in feed is shown below.

| Storage Conditions | Stability in feed (w/w % initial) | |
| --- | --- | --- |
| | Ivermectin | Protected Ivermectin |
| 7 days at 40° C. | 90 | — |
| 14 weeks at 40° C. | 82 | — |
| 4 weeks at 50° C. | — | 85 |

EXAMPLE 10

A blend is prepared by mixing the following components.
Ivermectin: 2 parts by weight
Alginic acid: 32.5 parts by weight
Starch (Directly compressible): 32.5 parts by weight
Magnesium hydroxide: 32.5 parts by weight
Magnesium stearate: 0.5 parts by weight The blend is then compressed on a suitable tablet machine to produce thin compacts which are then milled to produce granules of about 0.5 mm diameter. Alternatively the blend may be passed through a roller compacter followed by screening.

The granule is then incorporated into feed as described in Example 1.

EXAMPLE 11

A wet blend is prepared by mixing the following components.
A.I.V.: 20 parts by weight
Alginic acid: 40 parts by weight
Magnesium hydroxide: 40 parts by weight
Water: sufficient to granulate
The wet blend is treated as described in Example 1.

EXAMPLE 12

Preparation of Tablet Formulation

| Ingredient | Milligrams Per Tablet |
|---|---|
| Ivermectin granule | 1.5 |
| Bone meal flour | 300 |
| Microcrystalline cellulose | 500 |
| Flavor | 250 |
| Dibasic calcium phosphate | 739.5 |
| Magnesium stearate | 9 |

The active granule is blended with a portion of the dibasic calcium phosphate and then incorporated with the flavor, microcrystalline cellulose and bone meal flour. The mix is blended to ensure homogeneity of Ivermectin, the magnesium stearate added and mixing continued for 3 minutes before compression on a suitable machine. Each tablet contains 75 μg of Ivermectin.

EXAMPLE 13

Preparation of Capsule Formulation

| Ingredient | Milligrams per Capsule |
|---|---|
| Ivermectin granule as prepared in Example 9 | 10 |
| Starch | 109 |
| Magnesium Stearate | 1.0 |

The active ingredient, starch and magnesium stearate are blended together. The mixture is used to fill hard shell gelatin capsules of a suitable size at a fill weight of 120 mg per capsule.

EXAMPLE 14

Following the procedure of Example 1, a protected wet blend containing mocimycin was prepared. The protected wet blend was granulated and incorporated into mash or feed pellets containing 100 ppm of mocimycin. The stability was noted as follows (percentages of original after the indicated time period):

| In mash | 6 weeks | at 30° C. | 100% |
|---|---|---|---|
| | 6 weeks | at 37° C. | 99% |
| In pellets | 6 weeks | at 30° C. | 96% |
| | 6 weeks | at 37° C. | 83% |

The unprotected drug has a stability of less than 25% after 2 months at 37° C.

EXAMPLE 15

Following the procedure of Example 1 a protected wet blend containing goldinomycin was prepared. The protected wet blend was granulated and incorporated into feed. The stability is rated as follows:

| Storage Conditions | Stability (%) |
|---|---|
| 6 weeks at 37° C. | 97% |

What is claimed is:

1. A stable granular formulation for administration in feed or feed-like components comprising:
   (a) 0.1–70 parts by weight of Efrotomycin, Ivermectin, milbemycins, tylosin, AIV, antibiotic B-5050, antibiotic tetrahydro B-5050, mocimycin, dihydromocimycin, goldinomycin or a combination thereof;
   (b) 10–80 parts by weight of a polysaccharide gelling agent selected from the group consisting of alginic acid and its salts
   (c) 10–85 parts by weight of magnesium hydroxide.

2. The granular formulation of claim 1 wherein the amount of the compound is from 0.1 to 70% by weight of the granular formulation.

3. The granular formulation of claim 1 wherein the ratio of the components are:
   (a) 0.1–70 parts by weight of the compound;
   (b) 10–80 parts by weight of one or a combination of the polysaccharide gelling agents; and
   (c) 10–80 parts by weight of magnesium hydroxide.

4. The granular formulation of claim 1 wherein the ratio of the components are:
   (a) 2–40 parts by weight of the compound;
   (b) 20–50 parts by weight of one or a combination of the polysaccharide gelling agents; and
   (c) 20–85 parts by weight of magnesium hydroxide.

5. The granular formulation of claim 1 wherein the ratio of the components are:
   (a) 5–35 parts by weight of the compound;
   (b) 15–50 parts by weight of one or a combination of the polysaccharide gelling agents; and
   (c) 20–80 parts by weight of magnesium hydroxide.

6. The granular formulation of claim 1 wherein the ratio of the components are:
   (a) 5 parts by weight of the compound;
   (b) 47.5 parts by weight of one or a combination of the polysaccharide gelling agents; and
   (c) 47.5 parts by weight of magnesium hydroxide.

7. The granular formulation of claim 1 wherein the polysaccharide gelling agent is alginic acid, calcium alginate or a combination thereof.

8. A pharmaceutical composition comprising a pharmaceutically acceptable carrier and an effective amount of the granular formation according to claim 1.

9. The composition of claim 8 wherein the carrier is an animal feed and the compound in the granular formation is Efrotomycin, Ivermectin, A.I.V., mocimycin, or goldinomycin.

10. The pharmaceutical composition of claim 8 wherein the compound is efrotomycin.

11. The stable granular formulation of claim 1 wherein the compound is efrotomycin.

12. A process for preparing a stable granular formulation containing:
   (a) 0.1–70 parts by weight of a compound selected from a group consisting of Efrotomycin, Ivermectin, milbemycins, tylosin, AIV, antibiotic B-5050, antibiotic tetrahydro B-5050, mocimycin, dihydromocimycin and goldinomycin or a combination thereof;

(b) 10–80 parts by weight of a polysaccharide gelling agent selected from the group consisting of alginic acid and its salts and (c) 10–85 parts by weight of magnesium hydroxide, which comprises:

(1) preparing a wet blend of the components described in (a), (b) or (c) by mixing with a solvent selected from a group consisting of water, loweralkanol, lower alkanone or a mixture thereof;

(2) drying the blend; and (3) screening the blend to granules of desired sizes.

13. The process of claim 12 wherein the compound is Efrotomycin, Ivermectin, A.I.V., mocimycin, or goldinomycin.

14. The process of claim 12 wherein the ratio of the components are:

(a) 0.1–70 parts by weight of the compound;

(b) 10–80 parts by weight of one or a combination of the polysaccharide gelling agents; and (c) 10–80 parts by weight of magnesium hydroxide.

15. The process of claim 12 wherein the ratio of the components are:

(a) 2–40 parts by weight of the compound;

(b) 15–50 parts by weight of one or a combination of the polysaccharide gelling agents; and (c) 20–85 parts by weight of magnesium hydroxide.

16. The process of claim 13 wherein the ratio of the components are:

(a) 5–35 parts by weight of the compound;

(b) 15–50 parts by weight of one or a combination of the polysaccharide gelling agents; and (c) 20–80 parts by weight of magnesium hydroxide.

17. The process of claim 12 wherein the ratio of the components are:

(a) 5 parts by weight of the compound;

(b) 47.5 parts by weight of one or a combination of the polysaccharide gelling agents; and (c) 47.5 parts by weight of magnesium hydroxide.

18. The process of claim 12 wherein the polysaccharide gelling agent is alginic acid, calcium alginate or a combination thereof.

19. The process of claim 12 wherein the compound is efrotomycin.

* * * * *